US008663581B2

(12) United States Patent
Fu et al.

(10) Patent No.: US 8,663,581 B2
(45) Date of Patent: Mar. 4, 2014

(54) PRE-CONCENTRATOR AND METHOD OF USING THE SAME

(75) Inventors: Xiaoan Fu, Louisville, KY (US); Richard M. Higashi, Louisville, KY (US); Michael Nantz, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/431,054

(22) Filed: Mar. 27, 2012

(65) Prior Publication Data
US 2012/0252129 A1 Oct. 4, 2012

Related U.S. Application Data

(60) Provisional application No. 61/468,436, filed on Mar. 28, 2011.

(51) Int. Cl.
*G01N 27/62* (2006.01)
*G01N 1/22* (2006.01)
*G01N 1/02* (2006.01)
*G01N 1/00* (2006.01)
*G01N 27/00* (2006.01)

(52) U.S. Cl.
USPC .............................. 422/527; 422/500; 422/50

(58) Field of Classification Search
USPC .......................................... 422/527, 500, 50
See application file for complete search history.

(56) References Cited

FOREIGN PATENT DOCUMENTS

WO     WO 2011/049972     *     4/2011

OTHER PUBLICATIONS

Lin, Y., et al., Protocol for Collection and HPLC Analysis of Volatile Carbonyl Compounds in Breath, Clinical Chemistry, American Association for Clicnical Chemistry, Jan. 1, 1995, pp. 1028-1032, vol. 41, No. 7, Washington, D.C.
Corradi, M., et al., Aldehydes in Exhaled Breath Condensate of Patients with Chronic Obstrucctive Pulmonary Disease, American Journal of Respiratory and Critical Care Medicine, Jan. 9, 2003, pp. 1380-1386, vol. 167, No. 10.
Fuchs, P., et al., Breath Gas Aldehydes As Biomarkers of Lung Cancer, International Journal of Cancer, Jun. 1, 2012, pp. 2663-2670, vol. 126, No. 11,.
Wang, H., et al., Analysis of Low Molecular Weight Compounds by MLADI-FTICR-MS, Journal of Chromatography B: Biomedical Sciences & Applications, 2011, pp. 1166-1179, Elsevier, Amsterdam, NL.
Fu, X., et al., A Novel Microreactor Approach For Analysis of Ketones and Aldehydes in Breath, The Analyst, Sep. 6, 2011, pp. 4662-4666, vol. 136, No. 22.
Alfeeli, B., et al., "MEMS-Based Multi-Inlet/Outlet Preconcentrator Coated by Inkjet Printing of Polymer Adsorbents," Sensors and Actuators B 133, 2008, pp. 24-32.
Biswas, S., et al., "Nucleophilic cationization reagents," Tetrahedron Lett. 2010, pp. 1727-1729, vol. 51.
Deng, C., et al., "Determination of Acetone in Human Breath by Gas Chromatography-Mass Spectrometry and Solid-Phase Microextraction with On-Fiber Derivatization" J. Chromatogr. B 810, 2004, pp. 269-275.
Rexach, R., et al., "Quantification of O-glycosylation Stoichiometry and Dynamics Using Resolvable Mass Tags," Nature Chemical Biology, Sep. 2010, pp. 645-651, vol. 6.
Poli, D. et al., "Determination of Aldehydes in Exhaled Breath of Patients with Lung Cancer by Means of On-Fiber-Derivatisation SPME-GC/MS," J. Chromatogr. B, 878, 2010, pp. 2643-2651.
Lamos, S., et al., "Relative Quantification of Carboxylic Acid Metabolites by Liquid-Chromatography Mass-Spectrometry Using Isotopic Variants of Cholamine," Anal Chem. Jul. 15, 2007, pp. 5143-5149, vol. 79, No. 14.
Higashi, T., et al. "Determination of prostatic androgens in 10 mg of tissue using liquid chromatography-tandem mass spectrometry with charged derivatization," Anal Bioanal Chem, 2005, pp. 1035-1043, vol. 382.
European Patent Office, International Search report in related PCT/US2012/030837, dated Jun. 26, 2012, 13 pages.

* cited by examiner

*Primary Examiner* — Christine T Mui
(74) *Attorney, Agent, or Firm* — Wood, Herron & Evans, LLP

(57) ABSTRACT

A chemical pre-concentrator is provided having a support structure, an airflow conduit, and a layer of a reactive chemical compound on a surface of the support structure is used for collecting and pre-concentrating at least one chemical analyte from a dilute sample. A method of concentrating a gaseous sample is provide that includes exposing the chemical pre-concentrator with a dilute gaseous sample that contains at least one chemical analyte; and forming a conjugate of the at least one chemical analyte. A method of diagnosing a disease state in a mammalian patient is provided using the chemical pre-concentrator.

26 Claims, 13 Drawing Sheets

PRE-CONCENTRATOR AND METHOD OF USING THE SAME

CROSS-REFERENCE TO RELATED APPLICATIONS

This application claims benefit of and priority to prior filed and co-pending U.S. Provisional Patent Application Ser. No. 61/468,436 to Xiaoan Fu et al. entitled "PRE-CONCENTRATOR AND METHOD OF USING THE SAME," filed on Mar. 28, 2011, which is expressly incorporated by reference herein in its entirety.

FIELD OF THE INVENTION

The present invention is directed to chemical pre-concentrators, and more particularly, to chemoselective pre-concentrators, and methods associated therewith.

BACKGROUND OF THE INVENTION

The analysis of human breath samples promises to be a powerful non-invasive diagnostic tool for detecting many diseases, including lung cancer, diabetes, tuberculosis, heart disease, and chronic obstructive pulmonary disease (COPD). Breath is a complex mixture of atmospheric gases, water, and trace volatile organic compounds (VOCs) and nonvolatile compounds. The VOCs in breath are generally assumed to derive mainly from blood by passive diffusion across the pulmonary alveolar membrane. Gas chromatography coupled with a mass spectrometer detector (GC-MS) is currently the technique of choice for analysis of VOCs in breath. In 1971, Pauling first reported gas-chromatography (GC) for analysis of breath and his study revealed the presence of large numbers of VOCs in human breath. It is now known that breath contains at least 200 different VOCs that have been proposed as biomarkers for various disease states.

However, some of the critical challenges for breath analysis include that: many of the VOCs in breath range from only a few parts per trillion (ppt) to a few parts per billion (ppb) concentration; many chemical species in breath samples are at millions-fold higher concentration than VOCs, such as water vapor and carbon dioxide, which may need to be removed to avoid swamping most analytical instruments; breath is a very complex mixture containing more than 200 VOCs consisting of diverse mixtures of alcohols, ketones, and aldehydes, which complicates the identification of disease biomarkers; and VOCs in breath include non-metabolic constituents, which may introduce false biomarkers in breath analysis.

Thus, in order to efficiently and accurately analyze VOCs in breath, the first hurdle to overcome is that of concentrating the VOCs of interest. General approaches to concentrating one or more VOCs of interest from dilute gaseous samples have focused on one of the following: chemical, cryogenic, and adsorptive.

Chemical trapping has traditionally used "wet chemistry" where breath is bubbled through a reagent solution that captures a specific compound, such as ethanol or acetone. One disadvantage of the technique is that trace chemical loss is a problem in real breath sample analysis.

For cryogenic trapping, the volatile compounds are captured by condensing or freezing the VOCs in a cold trap. However, a cold trap may also freeze water and carbon dioxide, both of which are abundant in breath, and thus may plug the cold trap.

Adsorptive trapping is generally considered to be the most convenient and thus, the most widely used approach. In this method, VOCs are captured by binding them to adsorbent agents. Various adsorptive materials have been used as adsorbent in breath analysis, such as organic polymers (e.g., Tenax® TA), activated charcoal, graphitized carbon, and carbon molecular sieves (e.g., Carboxen™ 1021).

The majority of existing pre-concentrators trap VOCs by physical adsorption, with resulting low efficiency or speed. Attempts to enhance these physical adsorption pre-concentrators have included invoking high surface area construction, such as stainless steel or glass-capillary tubes packed with one or more granular absorbent materials. Other physical adsorption pre-concentrators have been fabricated on silicon wafers using micro-electromechanical system (MEMS) technology, which typically employ a micro-hotplate and an adsorption material layer deposited on the active area adjacent to the heating element. However, even these pre-concentrators have common physical adsorption efficiency and selectivity problems.

Further, a problem inherent to the physical adsorption methodology is that any increase in the efficiency of the adsorption step generally results in a lowered efficiency of the thermal desorption step to subsequently release the trapped VOCs. In view thereof, a need exists for new pre-concentrators to overcome the challenges of the prior art.

SUMMARY OF THE INVENTION

According to one embodiment, a chemical pre-concentrator for collecting and pre-concentrating at least one chemical analyte from a dilute gaseous sample is provided. The chemical pre-concentrator comprises a support structure having a surface; an airflow conduit directed at the surface of the support structure; and a layer on the surface of the support structure, where the layer comprises a reactive chemical compound having a general formula (I) of $$H_2N-Z-L-Y \qquad \text{Formula (I)}$$

wherein Z is NH, NR, or O; L is a linking group; Y is a di-substituted or tri-substituted N or P moiety; R is selected from the group consisting of alkyls, aralkyls, aralkenyls, and aralkynyls, each of which may be substituted or unsubstituted, and optionally contain one or more heteroatoms, wherein the reactive chemical compound is capable of forming a conjugate with the at least one chemical analyte to thereby retain the at least one chemical analyte on the surface of the support structure.

According to another embodiment, a method of concentrating at least one chemical analyte in a gaseous sample is provided. The method includes contacting the gaseous sample and a chemical pre-concentrator, wherein the chemical pre-concentrator comprises a reactive chemical compound; and forming a conjugate of the reactive chemical compound and the at least one chemical analyte to retain the at least one chemical analyte with the chemical pre-concentrator. The reactive chemical compound has the general formula of Formula (I).

According to yet another embodiment, a method of diagnosing a disease state of a mammalian patient is provided. The method includes obtaining a biological sample containing a biomarker from the mammalian patient, wherein the biomarker relates to the presence of a disease; contacting a chemical pre-concentrator with a gaseous sample containing at least a portion of the biological sample, wherein the chemical pre-concentrator comprises a reactive chemical compound; forming a conjugate of the reactive chemical compound and the biomarker to retain the biomarker with the chemical pre-concentrator; and performing analysis of the conjugate to identify or quantify the biomarker. The reactive chemical compound has the general formula of Formula (I). In one example, the performing analysis includes utilizing Fourier-transform ion cyclotron resonance mass spectrometry (FTICR-MS).

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to describe the invention.

DETAILED DESCRIPTION OF EMBODIMENTS OF THE INVENTION

Figure 1:
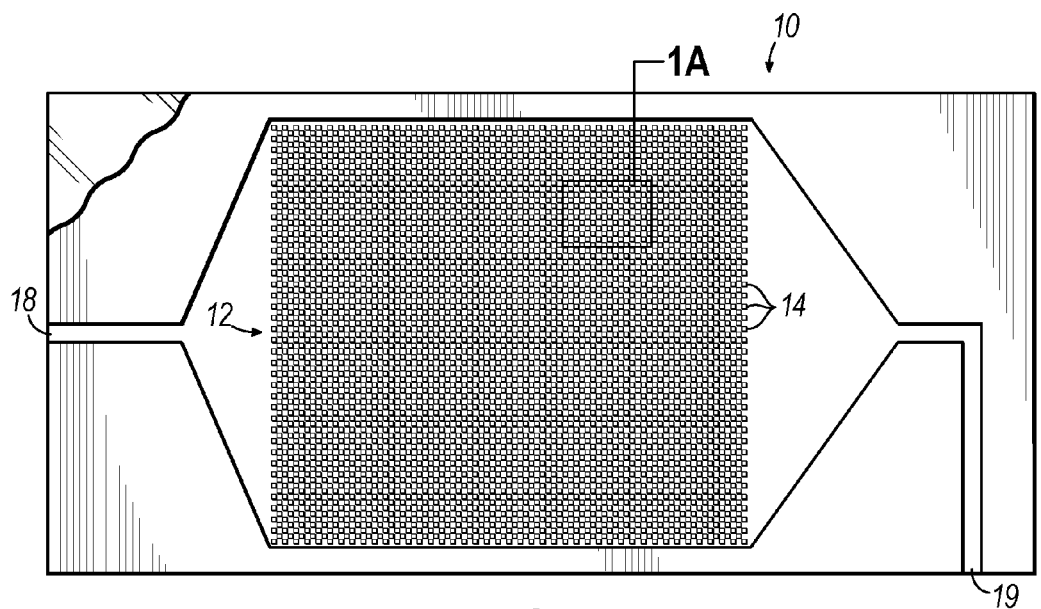
FIG. 1 is an illustrative drawing of a scanning electron microscope (SEM) optical micrograph of a fabricated chemical pre-concentrator according to an embodiment of the present invention.
Figure 1A:
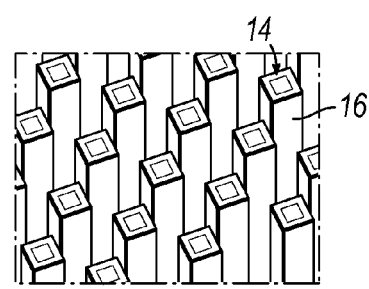
FIG. 1A is an expanded view of the region 1A of FIG. 1 showing micropillars in accordance with the embodiment shown in FIG. 1.

Embodiments of the present invention relate to a chemical pre-concentrator apparatus and methods of making and using the same. The chemical pre-concentrators of the present invention include a support structure and a layer of a reactive chemical compound on a surface of the support structure. As used herein, the phrase "reactive chemical compound" includes molecular compounds held together by covalent bonds and salts held together by ionic bonds.

Accordingly, embodiments of the present invention utilize a reactive chemical compound to form conjugates with at least one chemical analyte in order to affect the collecting and pre-concentrating of the at least one chemical analyte. In general terms, the reactive chemical compounds include a reactive terminus capable of reacting with a complementary functional group on the at least one chemical analyte of interest, an anchoring moiety capable of reversibly effecting the formation of a layer on the surface of the support structure, and a linking group between the reactive terminus and the anchoring moiety. As represented in Formula (I) below, the reactive terminus includes an amino group bonded to a heteroatom, and the linking group (L) and the anchoring moiety (Y) are as defined below.

In accordance with embodiments of the present invention The reactive chemical compound has a general formula according to that of Formula (I):

$$H_2N-Z-L-Y \qquad \text{Formula (I)}$$

wherein Z is NH, NR or O; L is a linking group; and Y is di-substituted or tri-substituted N or P moiety; R is selected from the group consisting of alkyls, aralkyls, aralkenyls, and aralkynyls, each of which may be substituted or unsubstituted, and optionally contain one or more heteroatoms.

According to an embodiment, Y can be $-NR^1R^2$, or $-NR^1R^2R^3$, $-PR^1R^2$, $-PR^1R^2R^4$, wherein $R^1$, $R^2$, $R^4$ are independently selected from the group consisting of alkyls, aralkyls, aralkenyls, and aralkynyls, each of which may be substituted or unsubstituted, and optionally contain one or more heteroatoms; and R³ is selected from the group consisting of H, alkyls, aralkyls, aralkenyls, and aralkynyls, each of which may be substituted or unsubstituted, and optionally contain one or more heteroatoms. In an alternative embodiment, R¹ and R² in combination can also form a heterocyclic ring, such as a piperidine or a morpholine moiety.

According to another embodiment of the invention, the reactive chemical compound may include a reactive terminus, a cationic moiety and a linking group L therebetween. When Y is —NR¹R²R³ or —PR¹R²R⁴, the reactive chemical compound is a cationic salt, which may further comprise ⁻A, which is an anionic counter-ion. Accordingly, the cationic moiety may comprise a cationic nitrogen, such as an ammonium ion, or a cationic phosphorus, such as a phosphonium. When Y is phosphorus, R¹, R² and R⁴ may all be an aryl group, such as phenyl. When Y is nitrogen, R¹, R² and R³ may be alkyls, each of which may be substituted or unsubstituted, and optionally contain one or more heteroatoms. In an alternative embodiment, when Y is nitrogen, R¹, R² may be alkyls, each of which may be substituted or unsubstituted, and optionally contain one or more heteroatoms, and R³ may be H.

According to embodiments of the invention, the reactive terminus may comprise a hydrazine or aminooxy group. For example, Z may be nitrogen, such as NH or NR, thereby forming a hydrazine terminus. Alternatively, Z may be oxygen, thereby forming an aminooxy terminus. The hydrazine or aminooxy termini form the reactive functional group of the reactive chemical compounds, and as such, the at least one chemical analyte includes at least one complementary functional group that will react therewith. Particularly reactive complementary functional groups include aldehydes and ketones.

The conjugation of the reactive chemical compound and the chemical analyte is based on the principle that each is a complementary reactant. According to embodiments of the present invention, the conjugates formed between the reactive chemical compounds of formula (I) are hydrazones (when Z=N) or oximes (when Z=O). In either conjugate form, the covalent bonding fixes the chemical analyte to the anchoring moiety and thereby pre-concentrates the chemical analyte prior to analysis.

In the reactive chemical compound, the linking group L covalently bonds the reactive terminus to the anchoring moiety. The reactive chemical compounds are not particularly limited by the linking group. However, increased substitution in the proximity of the reactive terminus may increase steric hindrance and thereby affect the reactivity of the compound. As such, varying the substitution may enable differentiation between aldehyde and ketone analytes, if desired. According to embodiments of the invention, the linking group may include a non-ionic segment, which may be a substituted or unsubstituted alkyl, a substituted or unsubstituted aryl, or an ether. For example, the linking group L may be ethyl, propyl, butyl, pentyl, hexyl, heptyl, or octyl segment. The linking group L may include an ether, such as polyethyleneglycol (PEG).

When the reactive chemical compound is a salt, the anionic member (A) of the reactive chemical compound is a negatively-charged species which counterbalances the positively-charged moiety. According to another embodiment, A may be a conjugate base of a strong acid. For example, A may be a halide such as bromide or chloride. According to another embodiment, A may be a conjugate base of a weak acid. For example, A may be a carboxylate such as benzoate. In one embodiment, Z is O, and Y is nitrogen, and the reactive chemical compound has a general formula according to that of Formula (II):

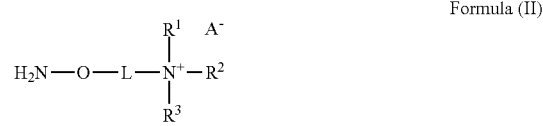

Formula (II)

where L, R¹, R², R³, and A are defined above. In another embodiment, at least one of R¹, R² and R³ is a methyl group and A is a halide.

It is also envisaged that the reactive chemical compound can include a plurality of reactive termini. For example, at least one of R¹, R² and R³ may be a substituted or unsubstituted alkyl including at least two heteroatoms, and having a general formula of -L¹-Z—NH₂, wherein L¹ is a linking group between an ammonium nitrogen and Z.

As shown in Scheme 1, an exemplary reactive chemical compound (4), according to Formula (II) where L is ethyl, may be realized via a three step synthetic sequence. An amino alcohol (1) may be converted to the corresponding phthaloyl-protected aminooxy ammonium salt (3) by first treating the amino alcohol (1) with N-hydroxyphthalimide (2) under Mitsunobu conditions, which is subsequently followed by quaternization using an alkyl halide (R³—X) to provide the protected salt (3). Removal of the phthaloyl group via hydrazinolysis affords the reactive compound (4). Exemplary reactive chemical compounds are shown in Table 1 below.

Scheme 1: Synthesis of aminooxy reactive compound (4).

TABLE 1

Exemplary reactive chemical compounds 4a-4e prepared according to a three-step synthetic sequence.

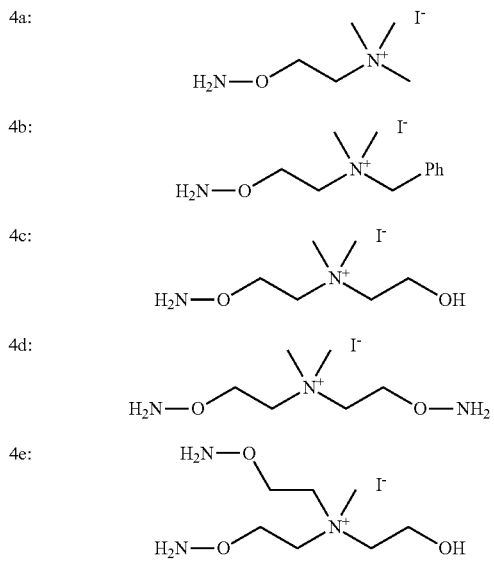

In yet another embodiment, Z is O, and Y is nitrogen, and the reactive chemical compound has a general formula according to that of Formula (III):

Formula (III)

The reactive chemical compounds in accordance with general Formula (III) can be prepared by omitting the quaternization step (2) in the synthetic sequence shown in Scheme I. For example, an exemplary reactive chemical compound according to Formula (III) where L is ethyl, may be realized via a two step synthetic sequence. Amino alcohol (1) may be converted to its corresponding phthaloyl-protected aminooxy by first treating the amino alcohol (1) with N-hydroxyphthalimide (2) under Mitsunobu conditions. Removal of the phthaloyl group via hydrazinolysis affords the tertiary amine reactive compound according for Formula (III). An exemplary tertiary amine reactive compound is N-(2-(aminooxy)ethyl)-morpholine (AMA).

According to an embodiment, the tertiary amine group can be used as an anchoring group. In an alternative embodiment, the tertiary amine reactive chemical compound may be converted to its Brønsted salt by treatment with a protic acid. For example, the tertiary amine reactive chemical compounds of Formula (III) can be dissolved in a suitable organic solvent and treated with an acid to prepare the reactive chemical compound of Formula (II), where $R^3$ is H, and A is the conjugate base of the acid.

The reactive chemical compounds may be dissolved in one or more solvents and then deposited on a surface of a support structure. The solvent is not particularly limited, but should be capable of evaporating while leaving the reactive chemical compound on the surface of the support structure. Suitable solvents include polar protic solvents, polar aprotic solvents, or combinations thereof. Exemplary polar protic solvents include, but are not limited to, water and alcohols, such as methanol. Exemplary polar aprotic solvents include, but are not limited to acetonitrile, dimethylformamide, dimethysulfoxide and nitromethane. The reactive chemical compound may be provided as a liquid, obtained by combining the reactive chemical compound and at least one solvent, which is then applied to a surface of a support structure. Removal of the solvent thereby deposits the reactive chemical compound on the surface of the support structure as a layer.

It should also be appreciated that the layer on the surface of the support structure may further include one or more substances that can facilitate physical adsorption of non-polar or weakly polar volatile organic compounds (VOCs). For example, the conjugate of reactive chemical compound 4d (N-(bis-2-(aminooxy)ethyl)-N,N-dimethylammonium iodide) with 2 molar equivalents of oleic aldehyde, i.e., N,N-dimethyl-2-(((Z)-((Z)-octadec-9-en-1-ylidene)amino)oxy)-N-(2-(((Z)-((Z)-octadec-9-en-1-ylidene)amino)oxy)ethyl) ethanaminium iodide, (ODM), can also be present in the layer on the surface of the support structure. The long carbon chain of the conjugated oleic aldehyde facilitates adsorption of non-polar or weakly polar VOCs.

The support structures of the chemical pre-concentrators, in accordance with embodiments of the present invention, provide a surface to which the reactive chemical compound can be retained after solvent removal. A binding force that contributes to retaining the reactive chemical compound on the surface of the support structure is the interaction between the anchoring moiety (e.g., ammonium group) portion of the reactive chemical compound and the functional groups on the surface of the support structure, such as hydroxyls, as discussed further below.

The configuration of the support structure is not particularly limited by any specific configuration, but when present, features such as, inlet and outlet structure, shapes and array patterns may affect the efficiency of the reactive chemical compound to capture the desired chemical analytes. Accordingly, the support structure may be configured to optimize surface area and flow dynamics.

Figure 2A:
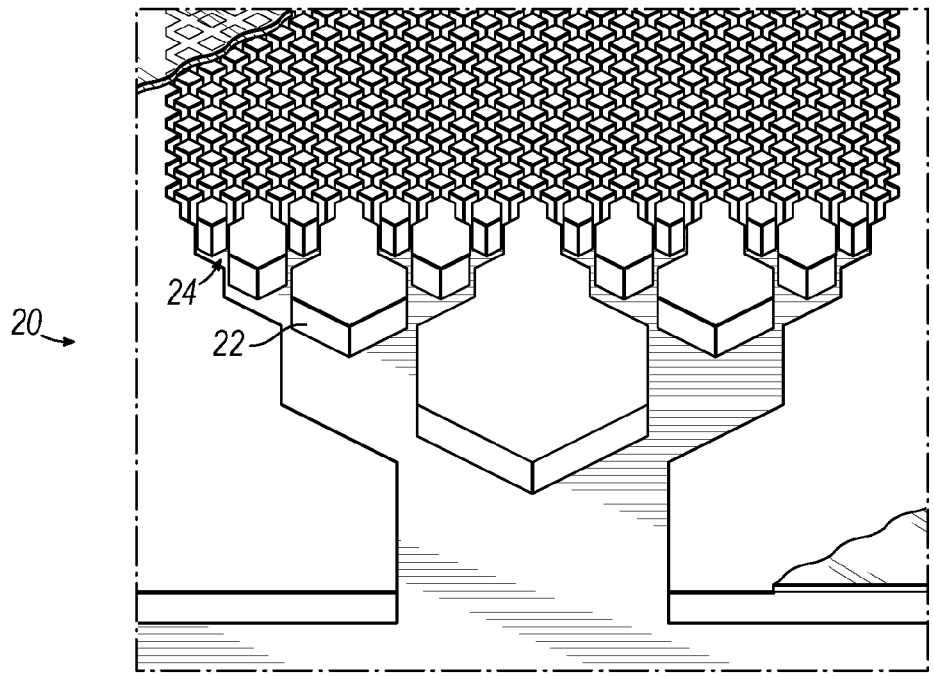
FIG. 2A is an illustrative drawing of a SEM micrograph of an inlet microstructure of a liquid chromatographic column suitable for use in a chemical pre-concentrator in accordance with another embodiment of the present invention.
Figure 2B:
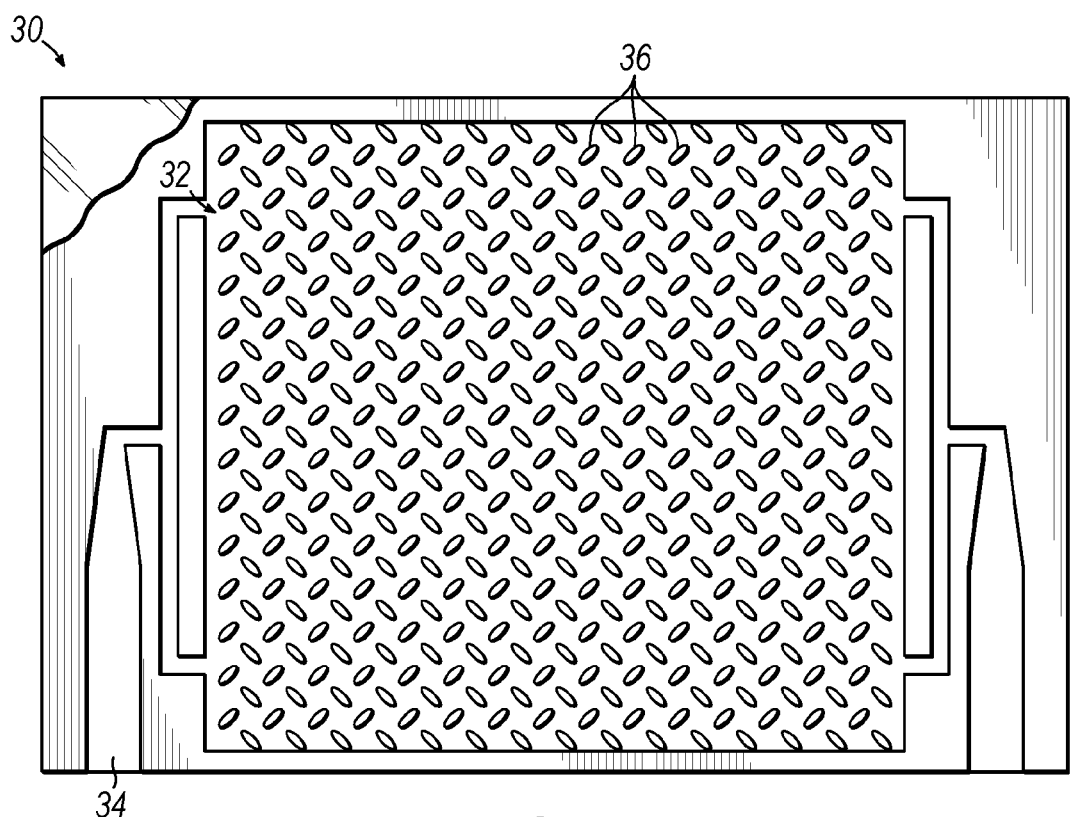
FIG. 2B is an illustrative drawing of a SEM micrograph of a chemical pre-concentrator with split inlet and outlet structures suitable for use in a chemical pre-concentrator in accordance with another embodiment of the present invention.
Figure 2C:
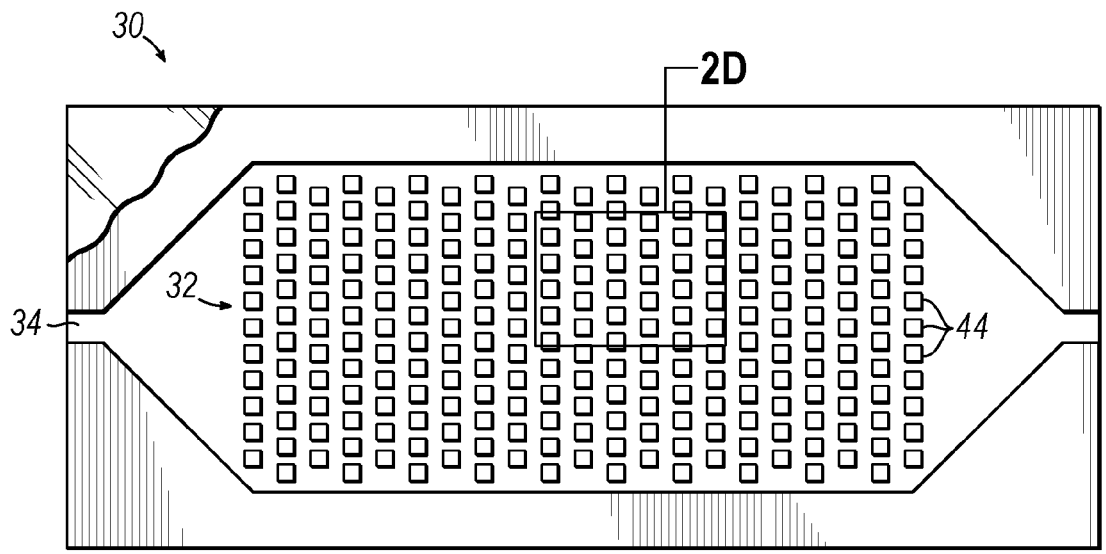
FIG. 2C is an illustrative drawing of a pre-concentrator in accordance with another embodiment of the present invention.
Figure 2D:
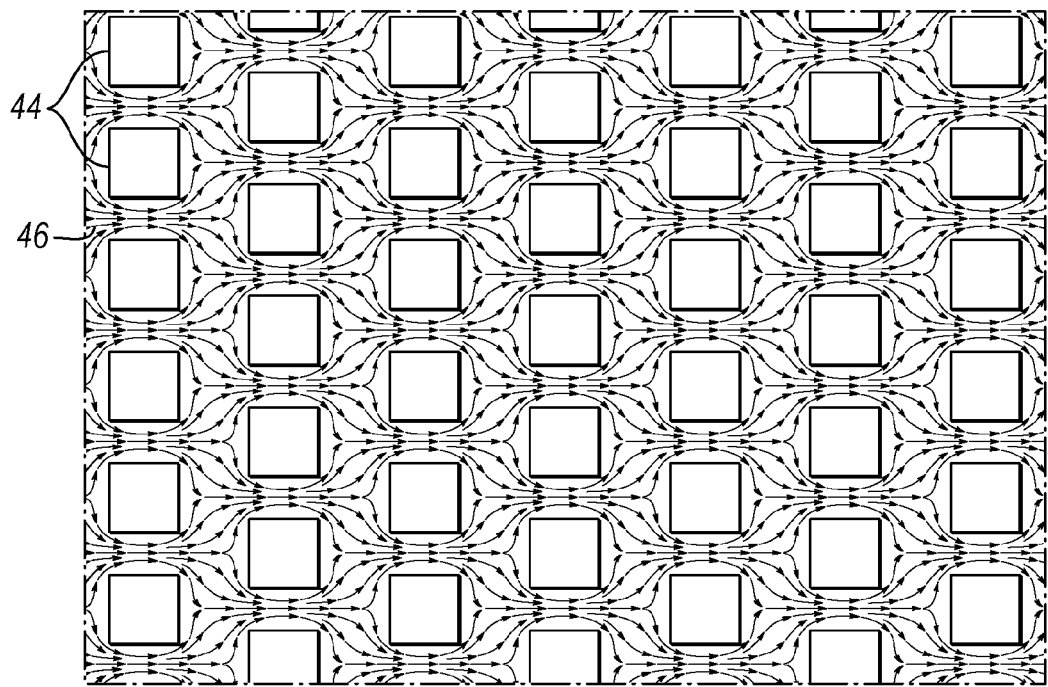
FIG. 2D is an expanded view of the region 2D of FIG. 2C showing an illustrative depiction of computation fluid dynamics (CFD) simulation of the chemical pre-concentrator embodiment shown in FIG. 2C.
Figure 3A:
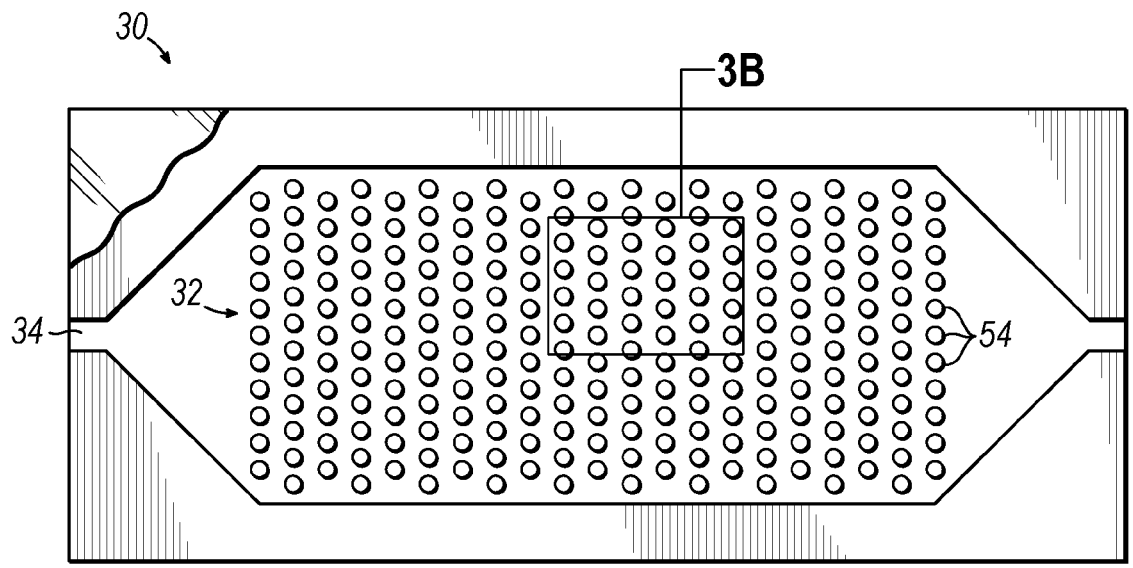
FIG. 3A is an illustrative drawing of a chemical pre-concentrator in accordance with another embodiment of the present invention.
Figure 3B:
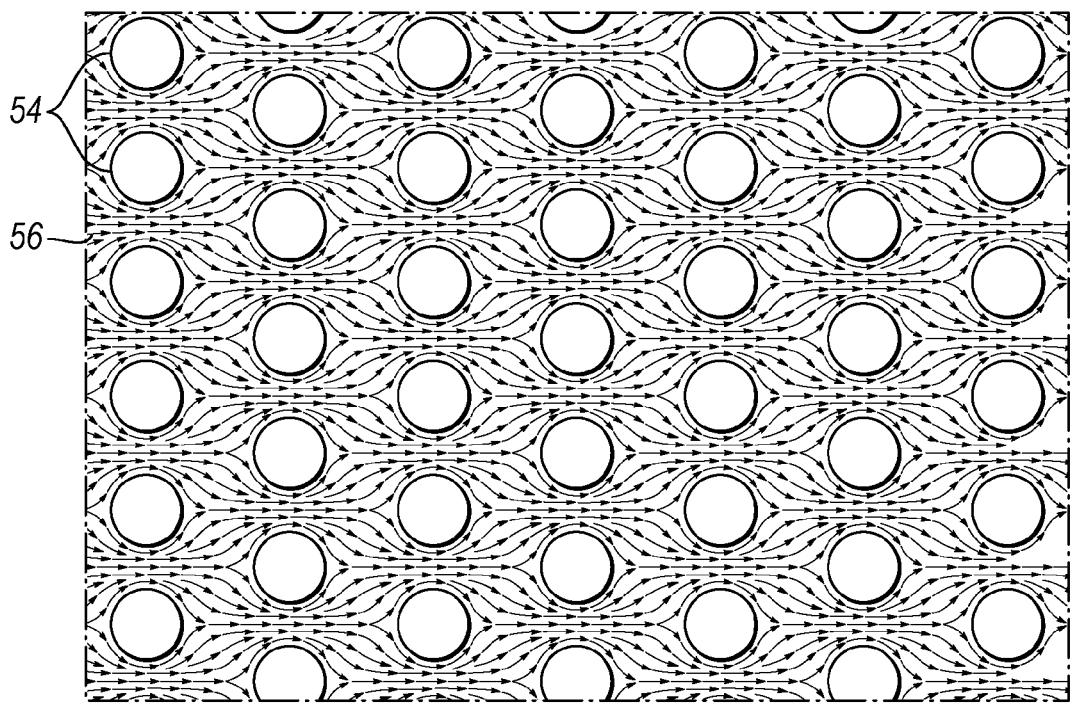
FIG. 3B is an expanded view of the region 3B of FIG. 3A showing an illustrative depiction of a simulated flow field in the chemical pre-concentrator with a cylindrical micropillar array shown in FIG. 3A.
Figure 3C:
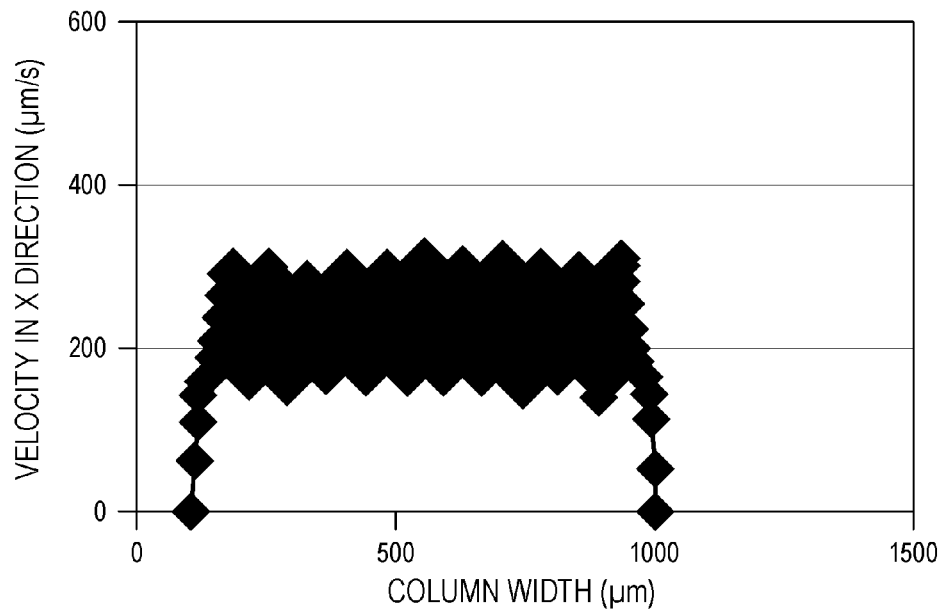
FIG. 3C is a graphical representation of flow velocity distribution across the chemical pre-concentrator embodiment shown in FIG. 3A.

In FIG. 1, an illustrative depiction of a scanning electron microscope (SEM) micrograph is shown of a fabricated pre-concentrator 10 according to one embodiment, wherein the support structure 12 is configured into micropillars 14 and coated with a layer 16 of the reactive chemical compound. The fabricated pre-concentrator 10 further includes an inlet airflow conduit 18 directed at the micropillars 14 on the support structure 12, and an outlet conduit 19. Other exemplary surface configurations of a pre-concentrator 20 that can be coated with layer 22 of the reactive chemical compounds include microchannels 24, which may be similar to a microstructure used in liquid chromatographic columns as shown in FIG. 2A (see He, B.; Tait, N.; Regnier, F.; "Fabrication of nanocolumns for liquid chromatography," Anal. Chem. 1998, 70, pp. 3790-3797), or pores. If desired, combinations of micropillars, microchannels, and/or pores may be employed. According to various embodiments, the micropillars may have different geometries. For example, a pre-concentrator 30 having a substrate 32 and an airflow conduit 34 can include elliptical micropillars 36 (FIG. 2B) (see Alfeeli, B.; Cho, D.; Ashraf-Khorassani, M.; Taylor, L. T.; Agah, M. "MEMS-based multi-inlet/outlet preconcentrator coated by inkjet printing of polymer adsorbents," Sensors and Actuators, 2008, 133, pp. 24-32), square micropillars (e.g., 44 of FIG. 2D), circular micropillars (e.g., 54 of FIG. 3B), rectangular micropillars (not shown), or combinations thereof may be employed depending on the desired flow dynamics.

The support structure may comprise any material that is compatible with the reactive chemical compound and is substantially insoluble in the solvent vehicle used to deposit the compound. More particularly, the surface of the support structure, which may be the same as or different from the underlying portion of the support structure, may comprise a material selected from the group consisting of dielectrics and semiconductors, which facilitates using MEMS techniques for manufacture, as exemplified in FIGS. 4A-4D and discussed below. For example, the surface material may be silicon, polycrystalline silicon, silicon oxide, silicon nitride, silicon oxynitride, silicon carbide, titanium, titanium oxide, titanium nitride, titanium oxynitride, titanium carbide, aluminum, aluminum oxide, aluminum nitride, aluminum oxynitride, aluminum carbide, or combinations thereof. Advantageously, the reactive chemicals compounds show exceptional binding to support structure surfaces comprising silicon oxide, titanium oxide, aluminum oxide, or combinations thereof.

Figure 5:
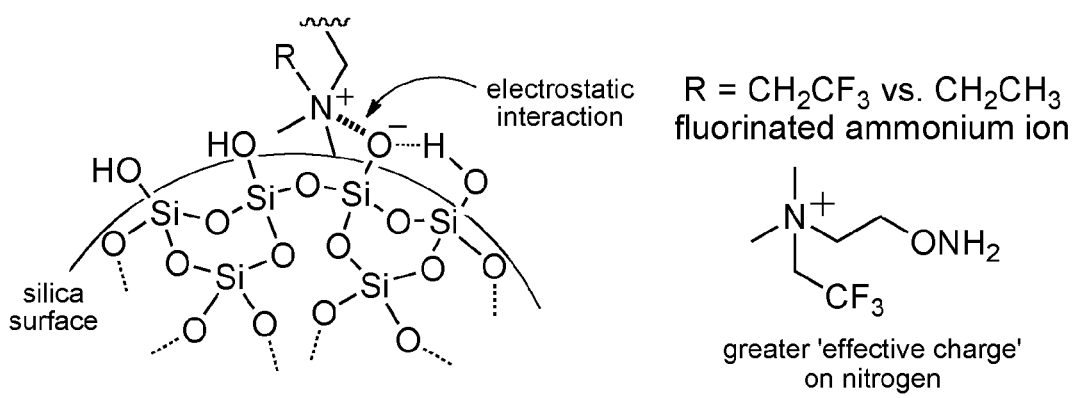
FIG. 5 is a schematic representation of a hypothetical surface interaction between silicon dioxide and ammonium salt functionality of a reactive chemical compound moiety.

The surface of the support structure may affect the binding forces for adhering the reactive chemical compound to the support structure. For example, the thermal oxidation of the silicon surface of the wafer or the deposition of silicon dioxide may control the density of silanol groups and/or the electrostatic charge on the $SiO_2$ surface of the micropillars. Without being bound by any particular theory, FIG. 5 provides a schematical representation of a possible surface interaction between silicon dioxide and the cationic moiety of an ammonium compound. It is believed that the hydroxyl groups, such as those found in silica, titania or alumina affect the adsorption and the reaction kinetics, capture efficiency, and desorption efficiency of reactive chemical compound and/or conjugate in cold solvent.

The chemical pre-concentrator may further comprise a housing surrounding the support structure, wherein the housing has an inlet and an outlet. According to an embodiment, the chemical pre-concentrator includes an airflow conduit directed at the surface of the support structure. Airflow conduits can include tubular devices which are not attached to the support structure, or maybe fabricated into the support structure. The outlet and/or the inlet may be configured to couple with a sampling pump to thereby facilitate the transfer of a portion of a gaseous sample outside of the housing into the housing through the inlet.

The reactive chemical compound may be applied to the surface of the support structure by any suitable method. In one embodiment, a liquid comprising a first solvent and the reactive chemical compound is contacted with the surface of the support structure and the first solvent is removed by evaporation under reduced pressure. If desired, the first solvent may be evaporated in a vacuum oven. For example, a dilute solution of a reactive chemical compound can be prepared from about 3.5 mg of the reactive chemical compound dissolved in about 0.5 mL of a first solvent, which simply acts as a carrier solvent. About 10 μL to about 20 μL of the dilute solution is applied to the pre-concentrator, and then the first solvent is removed under reduced pressure to afford a loading of approximately 0.07 to 0.14 mg of the reactive chemical compound into the pre-concentrator.

After the removal of the first solvent, the chemical pre-concentrator may be exposed to a dilute gas sample containing at least one chemical analyte having an aldehyde or ketone functional group. Upon reaction between the reactive chemical compound and the at least one chemical analyte, a conjugate thereof is retained on the surface of the support structure.

After the exposure is discontinued, the chemical pre-concentrator may be treated with a second solvent capable of dissolving the conjugate to remove the conjugate from the surface of the support structure and provide a concentrated sample of the conjugate. Suitable solvents include polar protic solvents, polar aprotic solvents, or combinations thereof. Exemplary polar protic solvents include, but are not limited to, water and alcohols such as methanol. Exemplary polar aprotic solvents include, but are not limited to, acetonitrile, dimethylformamide, dimethysulfoxide and nitromethane. If desired, this concentrated sample may be further concentrated by evaporating at least a portion of the second solvent.

At least a portion of the concentrated sample of the conjugated chemical analyte may be analyzed to identify and/or quantify the conjugate. One exemplary analytical tool is mass spectrometry, which may be performed with or without chromatography. For example, the conjugate may be analyzed using high performance liquid chromatography coupled with mass spectrometry (HPLC-MS) or gas chromatography coupled with mass spectrometry (GC-MS). Neutral chemical conjugates, such as those that can be obtained using tertiary amine reactive chemical compounds according to general Formula (III) are amenable to analysis using GC-MS. One beneficial feature of the tertiary amine reactive chemical compounds is their capability to be protonated with acid and form a positive charge, which is especially well-suited for analysis by Fourier transform ion cyclotron resonance-mass spectrometry (FTICR-MS), discussed below. By comparing FTICR-MS and GC-MS results, all ketones and aldehydes can generally be identified.

Where the reactive chemical compound utilized is a cationic salt according to general Formula (II), another useful method of analyzing the conjugate is FTICR-MS. The cationic functionality also imparts exceptionally high sensitivity for [+] ion FTICR-MS using nanoelectrospray techniques. This exceptionally high sensitivity enables detection limits in the femtomole to attomole ranges. This sensitivity is orders of magnitude better than even the most sensitive GC-MS, which generally requires 100-1,000 femtomoles or more for detection. Moreover, because the VOCs are rendered non-volatile, the final analytical solution can be concentrated (e.g., to dryness) and taken up by a very small amount of solvent. Additionally, nanoelectrospray FTMS only needs a few microliters of sample volume.

Moreover, FTICR-MS may also be coupled with chemical ionization (CI) or photo ionization (PI) and operated in negative [−] ion mode. Operating in [−] ion mode, rejects the cationic phase and permits the analysis of other chemicals retained in the chemical pre-concentrator. For example, the linking group L and/or R, $R^1$, $R^2$, $R^3$ may provide hydrophobic domains for pre-concentrating a broad spectrum of metabolic VOCs including C5 to C12 alkanes, alkenes and arenes. Moreover, additives may be included in the layer comprising the reactive chemical compound which will facilitate the capture of non-aldehyde or non-ketone-containing analytes. In either mode, the reactive chemical compound layer will be desorbed from the structure support surface of the pre-concentrator by dissolution with solvent followed by direct FTICR-MS analysis, completely eliminating the debilitating problem of traditional thermal desorption.

According to embodiments of the present invention, the chemical pre-concentrators may be used in many applications, such as in chemical weapons and explosives detection, environmental monitoring, industrial applications, and biological applications. The pre-concentrators may be used for monitoring air quality by analyzing the samples for the existence of and/or for quantifying a chemical analyte of interest.

Moreover, the chemical pre-concentrators may be used to detect and/or quantify biomarkers of diseases in biological samples, such as breath, which enable clinical diagnosis of various disease states.

Figure 4A:
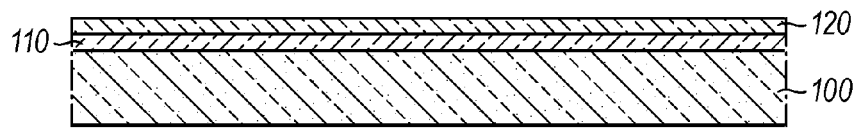
FIGS. 4A-4D illustrates a fabrication process flow showing a manufacturing process for a pre-concentrator support structure in cross-sectional view, according to an embodiment of the present invention.
Figure 4B:
Figure 4C:
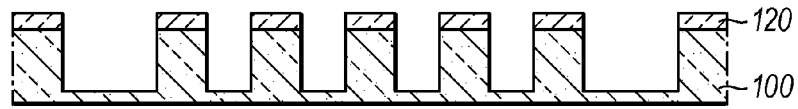
Figure 4D:
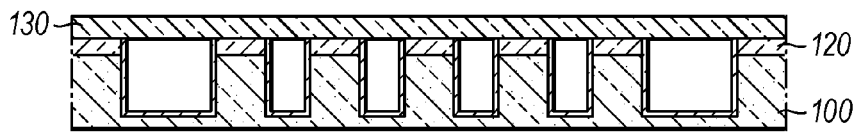

To construct a chemical pre-concentrator according to an embodiment of the present invention, MEMS techniques may be employed to manufacture the support structure. In reference to FIG. 4A, a surface of a silicon wafer 100 is thermally oxidized to form a 0.5 pµm $SiO_2$ thin film 110 as a deep reactive ion etching (DRIE) mask. Then, a photo resist layer 120 is formed on the $SiO_2$ surface 110 of the wafer 100. After imaging and developing a first pattern in the photo resist layer 120, the DRIE mask layer is patterned by buffered oxide etching (BOE) solution to transfer the first pattern through the DRIE mask, as shown in FIG. 4B. Micropillars for the chemical pre-concentrator are formed by a DRIE step, as shown in FIG. 4C. Next, the wafer 100 may be oxidized to form a 50 nm $SiO_2$ layer 110 using a "wet" $O_2$ and $H_2O$ atmosphere in a thermal oxidation furnace. If desired, the wafer 100 may be sealed by anodic bonding a glass wafer 130 to the support structure, to enclose the microchannels/micropillars, as shown in FIG. 4D. Additional processing to partition the processed wafer 100 may be performed as necessary to form chemical pre-concentrators of the desired dimensions and to open connection ports. In an alternative embodiment, the glass wafer 130 is omitted to provide an open-form of the pre-concentrator, which is suitable for capturing carbonyl compounds and other reactive compounds in exhaled breath by directly blowing breath gas on the chips using a small tube.

According to the above general procedure, a support structure for a chemical pre-concentrator was manufactured to demonstrate capturing trace aldehydes and ketones. A support structure having square prism micropillars was fabricated on a silicon wafer. FIG. 1 shows an illustrative depiction of an optical micrograph of the pre-concentrator support structure. Accordingly, the pre-concentrator was fabricated in a clean room to feature the desired flow channel size, which can be about 7 mm×about 5 mm, or about 14 mm×about 14 mm, for example. According to an exemplary embodiment, a closed-form (glass wafer sealed) pre-concentrator (14 mm×14 mm) with the micropillar array was prepared.

Depending on the flow characteristics (e.g., 46 and 56 of FIGS. 2D and 3B, respectively) and overall surface area desired, the micropillars may be oriented, sized, and/or shaped accordingly. For example, the micropillars of the pre-concentrator can be about 50 µm×about 50 µm to about 100 µm×about 100 µm square shape, or 50 µm in diameter cylindrical shape; the height of the micropillars can be from about 200 µm to 500 µm, or the distance between two micropillars can be about 50 µm. According to one embodiment, there are more than 5000 micropillars in the 14 mm×about 14 mm pre-concentrator. If the micropillar size and distance between two micropillars is decreased, the surface area of the pre-concentrator can be increased.

EXAMPLES

Synthesis of a Reactive Chemical Compound:

N-(2-(aminooxy)ethyl)-N,N,N-trimethylammonium iodide (ATM): To a solution of triphenylphosphine (15.3 g, 58.3 mmol) and N-hydroxyphthalimide (9.50 g, 58.3 mmol) in THF (200 mL) at 0° C. was added dropwise N,N-dimethylethanolamine (4.33 g, 48.6 mmol). After stirring 30 min, diisopropyl azodicarboxylate (DIAD) (11.5 mL, 58.3 mmol) was added slowly via syringe. The reaction mixture was stirred an additional 30 min at 0° C. and then allowed to warm to room temperature. After 12 h, the solvent was removed by rotary evaporation. EtOAc (150 mL) was added to dissolve the residue followed by successive washings with saturated aq. $NaHCO_3$ (3×100 mL), water (50 mL), and brine (3×100 mL). The organic layer then was dried ($Na_2SO_4$), filtered, and concentrated to approximately 50 mL by rotary evaporation. The organic layer was cooled using an ice bath and cold 5% aq. HCl (30 mL) was added. On complete addition, the mixture was warmed to room temperature and stirred 20 min. The aqueous layer was separated, washed with $Et_2O$ several times, cooled to 0° C., and then made alkaline by slowly adding saturated aq. $NaHCO_3$. The alkaline aqueous layer was extracted using chloroform (3×50 mL). The combined organic phase was dried ($Na_2SO_4$), filtered, and the solvent removed by rotary evaporation to afford the corresponding aminooxy phthalimide (8.53 g, 75%) as a light yellow solid which required no further purification for use in the next step; $^1$H NMR (DMSO-$d_6$, 500 MHz) δ 7.82 (d, J=5.0 Hz, 4H), 4.21 (t, J=5.0 Hz, 2H), 2.60 (t, J=5.0 Hz, 2H), 2.17 (s, 6H); $^{13}$C NMR (DMSO-$d_6$) δ 163.7, 135.3, 129.2, 123.8, 76.1, 57.4, 45.9.

The phthalimide (0.50 g, 2.13 mmol) was placed in a sealed tube and iodomethane (6.5 mL) was added. The mixture was degassed using a stream of nitrogen and then the tube was sealed and warmed to 50° C. After 2 h, the sealed tube was cooled, opened, and the solvent was evaporated (caution: fume hood required) to afford the crude ammonium iodide as a light yellow solid; $^1$H NMR (DMSO-$d_6$, 500 MHz) δ 7.89 (s, 4H), 4.67 (br s, 2H), 3.8 (t, J=5.0 Hz, 2H), 3.24 (s, 9H); $^{13}$C NMR (DMSO-$d_6$) δ 164.0, 135.9, 129.4, 124.3, 72.3, 64.2, 54.2.

The crude iodide compound was dissolved in a mixture of EtOH (5 mL) and $H_2O$ (0.05 mL). Hydrazine monohydrate (1.13 mL, 14.9 mmol) was added and the reaction mixture was stirred 4 h at room temperature. The solvents were removed by rotary evaporation and the residue was dissolved in $H_2O$ (15 mL). The aqueous solution was washed several times with EtOAc and then the $H_2O$ was evaporated by freeze drying to yield the title aminooxy compound (ATM) (0.41 g, 78%) as a light yellow amorphous solid: mp 97-99° C.; IR (DRIFT) 3236, 3008, 1480, 963 cm$^{-1}$; $^1$H NMR (DMSO-$d_6$, 500 MHz) δ 6.23 (s, 2H), 3.91 (br s, 2H), 3.52 (br s, 2H), 3.07 (s, 9H); $^{13}$C NMR (DMSO-$d_6$) δ 69.3, 64.1, 54.0. HPLC analysis ($C_{18}$ 5 µm column, gradient elution using 100% $H_2O$ to 100% $CH_3CN$ over 10 min at a flow rate of 1 mL/min) indicated excellent sample homogeneity (98% purity, $t_r$=1.88 min). The elution profile was monitored by UV absorbance at 214 nm. HRMS calculated for $C_5H_{15}N_2O^+$ (M$^+$): 119.1179, found: 119.1178.

Preparing and Testing a Chemical Pre-Concentrator:

A methanol solution of ATM was deposited on the surface of a micropillar array. Accordingly, about 0.07 to 0.14 mg of ATM was loaded into the micropillar array of a pre-concentrator using about 10 µL to about 20 µL of a dilute ATM solution prepared from 3.5 mg ATM dissolved in about 0.5 mL of methanol. After evaporating the methanol solvent and drying in a vacuum oven (e.g., ambient to 50° C.; 760 torr to 2 torr; and 1 to 5 hours), the chemical pre-concentrator was connected to an ultra high purity helium stream at a helium flow rate of 25 sccm followed by injection of deuterated (d6) acetone into the flow stream to produce an equivalent of 5 parts per million volume (ppmv) acetone-d6 in helium after 10 minutes of flow through the pre-concentrator. The reacted ATM phase containing the conjugate was then stripped from the micropillar surface of the pre-concentrator by simple methanol elution. For example, a slightly pressurized (e.g., greater than atmospheric pressure) vial containing methanol supplied methanol to the pre-concentrator, where another vial at a lower pressure (e.g., atmospheric pressure) collected the eluted conjugate sample. The two vials and the pre-concentrator were connected via fused silica tubing.

Figure 6:
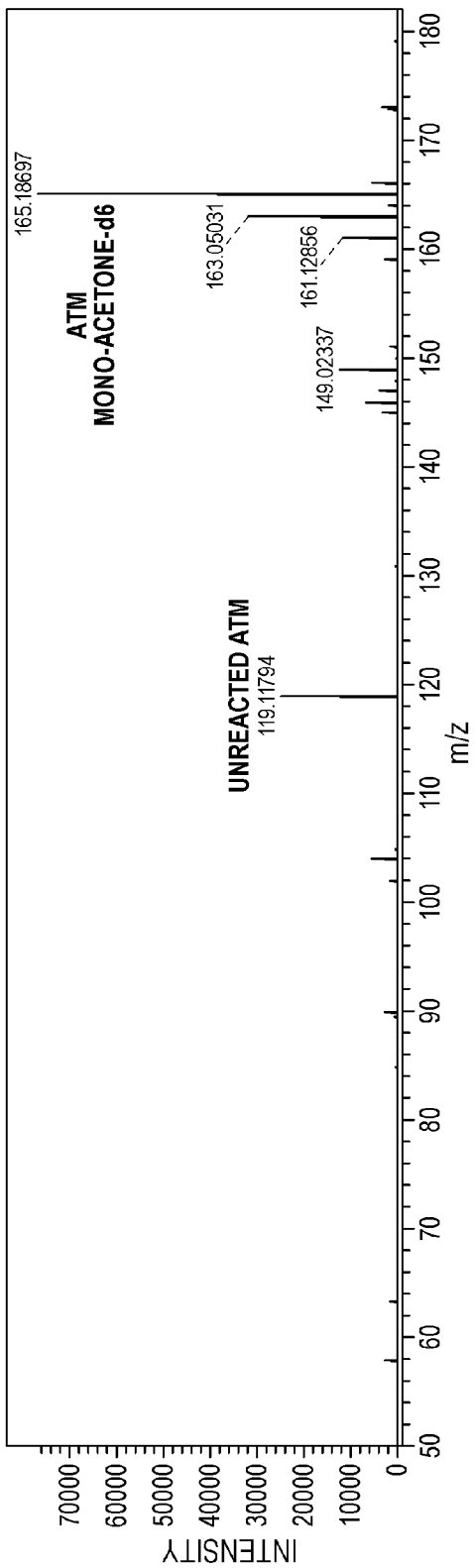
FIG. 6 depicts an FTICR-MS spectrum of 2-(aminooxy) ethyl-N,N,N-trimethylammonium (ATM) eluate from an ATM-coated chemical pre-concentrator after exposure to deuterated (d6) acetone.

The eluate was directly analyzed, with no further sample processing, by nano-electrospray FTICR-MS. The FTICR-MS spectrum in FIG. 6 shows a spectral region that has the oximation product of ATM bound to acetone-d6 (165.18697 mass ion), as well as unreacted ATM (119.11794 mass ion). Acetone-d6 was used to distinguish from any laboratory trace acetone contamination. In this case, there was no such contamination. The calculation from the FTICR-MS spectrum indicated that 98% deuterated acetone was captured by ATM. Both reacted and unreacted (excess) ATM were readily eluted from the pre-concentrator channel by methanol. There was no evidence of free (unreacted) acetone-d6 in the FTICR-MS spectrum, which demonstrates that the ATM-modified pre-concentrator was very effective at capturing a representative ketone and the conjugate can be stripped from the pre-concentrator by simple elution using cold solvent.

Figure 7:
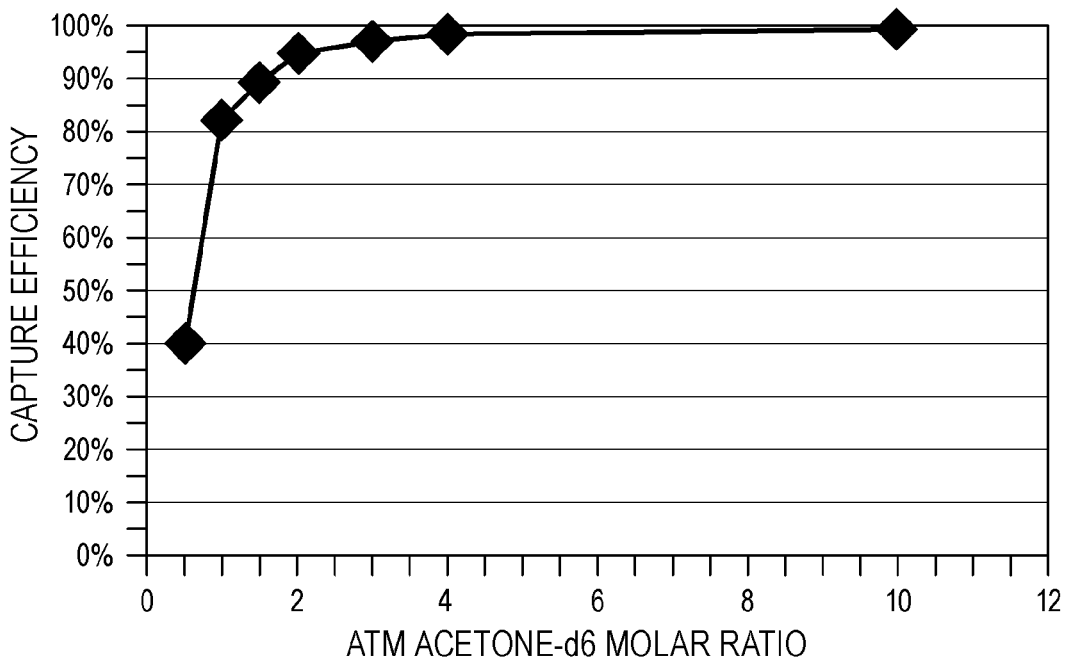
FIG. 7 is a chart illustrating the relationship between the Capture Efficiency (CE) versus the molar ratio of ATM to deuterated (d6) acetone (ATM/acetone-d6) in a chemical pre-concentrator in accordance with an embodiment.

FIG. 7 shows the capture efficiencies of ATM modified pre-concentrator shown in FIG. 1 for acetone-d6. The capture efficiency may be affected by the molar ratio of ATM to acetone. For example, as the molar ratio increased to larger than 5:1, the capture efficiency achieved 99% under the same operating conditions. This high efficiency (>95%) enables the detection and analysis of trace aldehydes and ketones, at parts per billion volume (ppbv) to parts per trillion volume (pptv) levels. Further, the chemoselectivity of the reactive chemical compounds will "filter out" interfering, non-biologically relevant species in breath, such as water and carbon dioxide while pre-concentrating the target VOCs thousands of times to easily match the detection range of FTICR-MS.

Coupling the various embodiments of chemical pre-concentrators of the present invention with the FTICR-MS platform provides a rapid (seconds), highly sensitive (femtomoles) analytical tool, which can simplify the complexity of lung disease biochemistry and biomarkers. Moreover, analyzing the isotopically-labeled metabolites of isotopically-labeled probes provides valuable insight to biological processes, but may also complicate the analysis of the metabolites. However, the combination of the instant chemical pre-concentrators and FTICR-MS platform accommodates extremely complex patterns of isotopic labeling, such as Carbon-13 labeling.

Testing a Chemical Pre-Concentrator with an Experimental Matrix:

According to an embodiment, the chemical pre-concentrators of the present invention may be used in analyzing breath for clinical diagnosis. Ketone and aldehyde metabolites are invariably produced in biochemical pathways as intermediates due to their reactive nature. Many of these are unique to a given pathway. They are also generated from oxidative reactions such as lipid peroxidation as a result of oxidative stress. Virtually all of the central metabolic pathways such as glycolysis, Krebs cycle, pentose phosphate pathway, metabolism of nucleic acid, sugar nucleotides, amino acids/proteins, fatty acids/lipids, carbohydrates, one-carbon transfer involve keto and/or aldehydic intermediates. Therefore, quantitative analysis of all ketone and aldehydic metabolites is important for noninvasive diagnosis. The exquisite selectivity of the aminooxy group ($H_2NO-$) and/or hydrazide group ($H_2NNH-$) for reaction with aldehyde and ketone carbonyl groups permits the chemoselective pre-concentration of chemical analytes bearing these functional groups.

Figure 8:
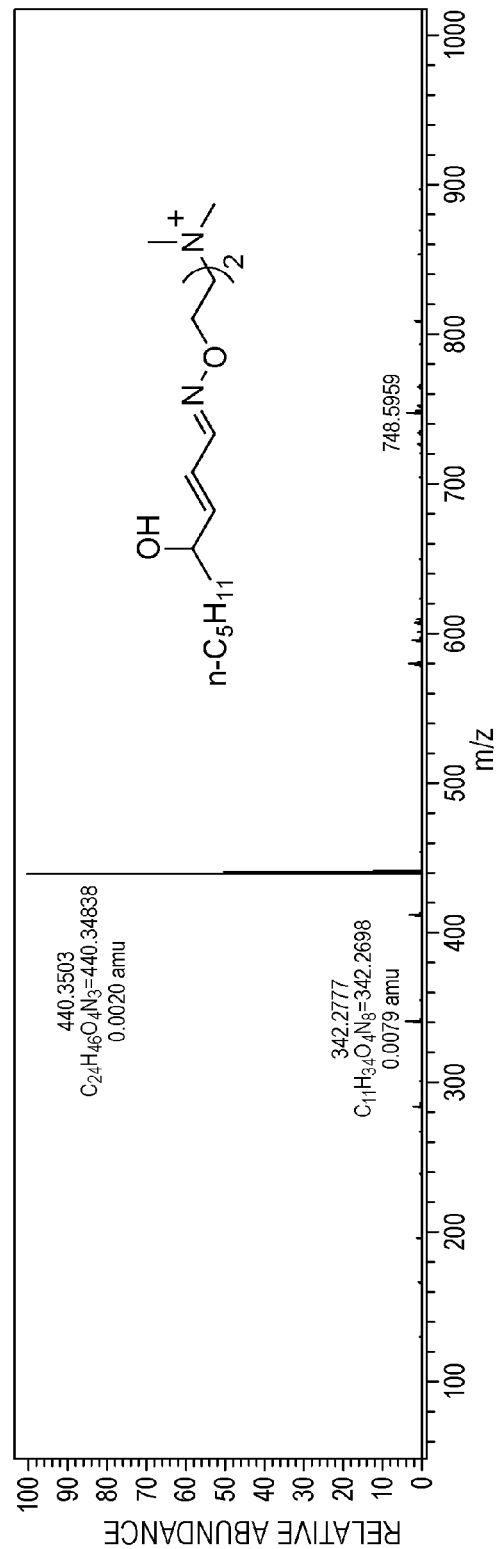
FIG. 8 is a mass spectrogram of a direct-infusion nanoelectro-spray FTICR-MS analysis of 4-hydroxynonenal (4-HNE) conjugated with bis(2-(aminooxy)ethyl)-N,N-dimethylammonium (bis-ADM) (440.3503 mass ion)

The concentrations of ketones and aldehydes in breath result from oxidative damage of metabolites such as lipids, and thus are early-warning indicators of lung cancer and chronic obstructive pulmonary disease (COPD). Representative aldehyde and ketone metabolites in combination with model reactive chemical compounds were tested to verify the fundamental operation of the method. Aldehydes, such as 4-hydroxynonenal (4-HNE), as well as ketone metabolites of glycolysis and the Krebs cycle, including sodium pyruvate, oxaloacetate, a-ketoglutarate were reacted with reactive chemical compounds. All gave the predicted bis(oxime ether) derivatives as per FT-ICR-MS analysis. FIG. 8 illustrates an example of the FTICR-MS spectrum of the bis(oxime ether) derivative of 4-HNE, a key lipid peroxidation product with bis(2-(aminooxy)ethyl)-N,N-dimethylammonium (bis-ADM) which bears two aminooxy groups. The FTICR-MS spectrum of FIG. 8 was obtained by direct-infusion nano-electro-spray FT-ICR-MS, and the proposed structure was consistent with mass ion fragments detected in Tandem MS analysis of this ion.

Figure 9A:
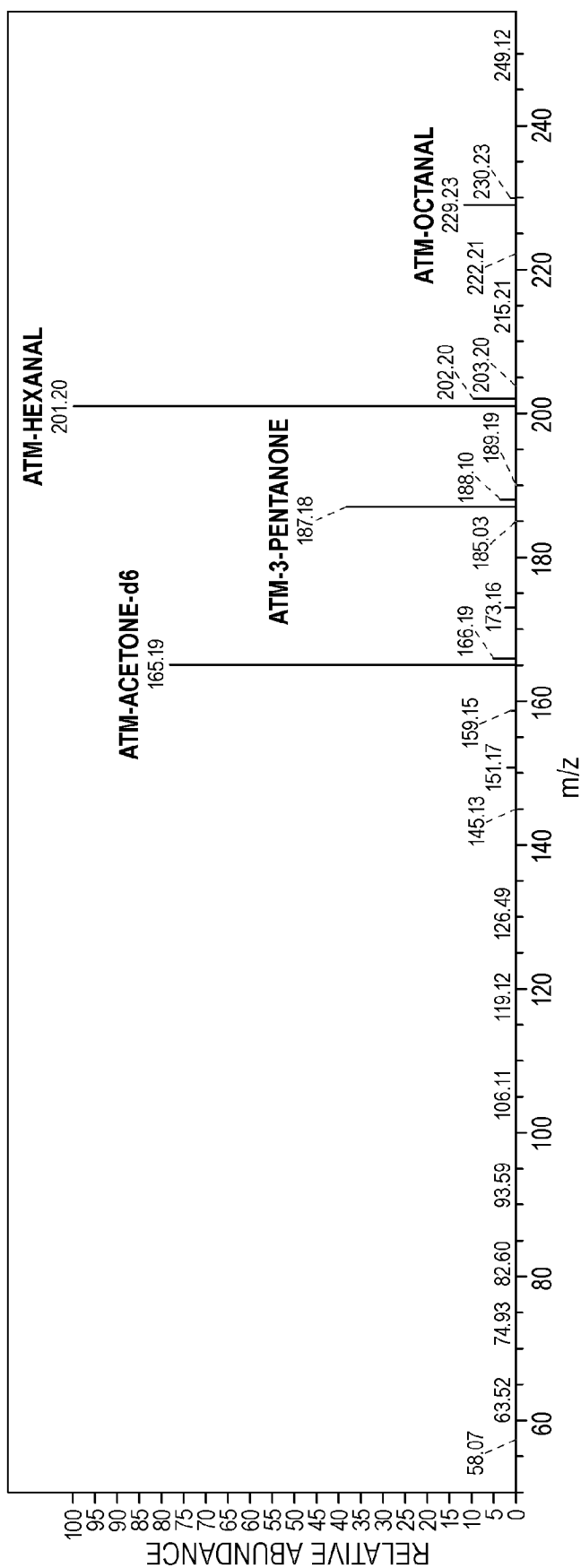
FIG. 9A is a mass spectrogram showing an FTICR-MS spectra of pre-concentrated samples using ATM-modified chemical pre-concentrators with ketones and aldehydes in helium mixtures at about 5 ppmv.
Figure 9B:
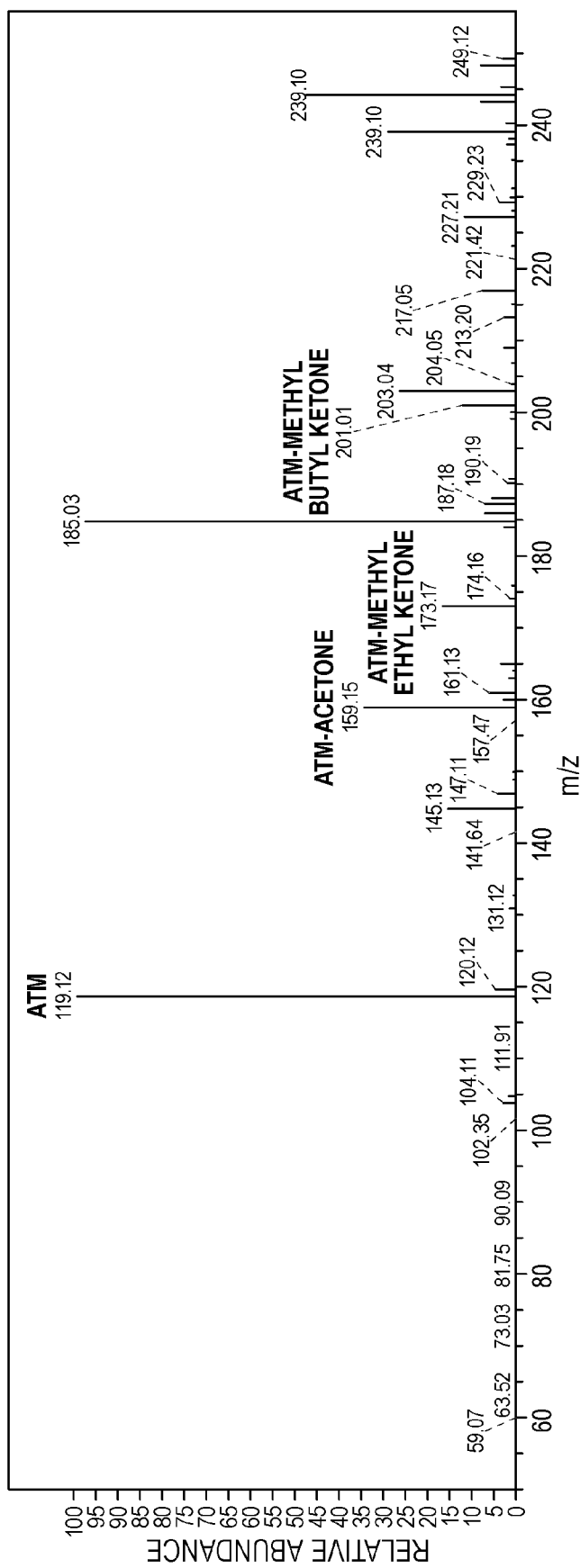
FIG. 9B is a mass spectrogram showing an FTICR-MS spectra of a pre-concentrated sample using ATM-modified chemical pre-concentrator with diluted TO-15 gas mixture with 1 ppbv acetone.

One skilled in the art will appreciate that the capture efficiency depends on pre-concentrator microstructure, the reactive chemical compound structure, and operation conditions. Further, the capture efficiency will also be affected by the oximation reaction kinetics, which is also affected by the structure of the aldehyde or ketone. Based on above results, the capture efficiencies of acetone-d6, pentanone, hexanal and octanal mixtures were tested and compared by flowing ultra high purity He carrier gas with Doppler-microflow controllers through a vessel containing these compounds to create an equivalent 5 ppmv for each ketone and aldehyde. The mixtures then flow through an ATM-modified pre-concentrator. FIG. 9A shows the FTICR-MS spectrum of the pre-concentrated aldehydes and ketones. The pre-concentrator successfully captured all aldehydes and ketones with different capture efficiencies. To further understand the interference of a large number of polar and nonpolar compounds including water on ATM capturing of aldehydes and ketones at ultra low concentrations, a standard organic TO-15 gas mixture for air quality calibration made by Spectra Gases was diluted to include 1.3 ppbv acetone and 1 ppbv methyl ethyl ketone by Entech 4600A Automated Dynamic Diluter. This TO-15 has 78 polar and nonpolar VOCs including methyl acetate and aromatic compounds. FIG. 9B shows the FTICR-MS spectrum of the pre-concentrated sample by an ATM modified pre-concentrator. Recovery experiments showed that 97% of acetone has been captured and detected by FTICR-MS while 87% methyl ethyl ketone and 81% methyl butyl ketone were captured. This result demonstrates that ATM can pre-concentrate ultra low level ketones at slightly different capture efficiencies.

Testing Protocol for Breath Analysis Using a Closed-Form Pre-Concentrator:

Exhaled breath samples are collected from healthy non-smokers, healthy smokers (as controls) and lung cancer patients using one-liter Tedlar® bags (Supelco, Bellefonte, Pa.) and a closed-form pre-concentrator having an inlet configured with a flow meter, and an outlet configured with a diaphragm (oil free) vacuum pump. An isolation valve and pressure gauge are positioned between the outlet and the pump. Ambient VOCs in the testing environment at the point of collection are also determined by obtaining paired air samples. The Tedlar® bags are tested free of VOC contamination after repeated nitrogen purging and evacuation cycles. Tidal breath samples are collected and used for analysis of VOCs.

After collecting 1 liter of exhaled breath, the Tedlar® bag is connected to the inlet of the pre-concentrator through a septa and fused silica tube. The outlet of the pre-concentrator is connected to the vacuum pump. The breath sample flows through the pre-concentrator from the Tedlar® bag. After the breath sample is evacuated, the pre-concentrator is disconnected. The reactive chemical compound coating phase and its capture adducts in the pre-concentrator are eluted by methanol and analyzed using mass spectrometry, such as FTICR-MS and GC-MS.

In an alternative embodiment, an open-form of the pre-concentrator without a glass cover is provided. The pre-concentrator design, features and fabrication can be similar to those aspects described above. Open form pre-concentrators permit capture of carbonyl compounds and other reactive compounds in exhaled breath by directly blowing breath gas on the open form pre-concentrators using a small tube, such as a drinking straw. Therefore, the open form pre-concentrator approach for sampling breath does not require any breath collection bag such as a Tedlar® bag and can eliminate a long durations (e.g., several hours) of flowing breath gas sample from the bag. The open-form pre-concentrator can also be used for sampling headspace gas of cell, tissue culture and bacterium culture and air quality monitoring.

The reactive chemical compounds suitable for use in the open form pre-concentrator may be the same as those used in the closed form. For example, the reactive chemical compound can be a positively-charged quaternary aminooxy compounds of general Formula (II), such as ATM; neutral aminooxy compounds of general Formula (II), such as AMA. The layer comprising the reactive chemical compound may further include conjugates of bis-aminooxy compounds with long chain aldehydes, such as ODM, to enable concentrating non-polar or weakly polar VOCs.

Testing Protocol for Breath Analysis Using an Open-Form Pre-Concentrator:

Exhaled breath samples are collected from a healthy (non-cancerous) smokers (as control) and a lung cancer patient. Ambient VOCs in the testing environment at the point of collection are also determined by obtaining paired air samples. Both subjects provided two breath samples by blowing breath gas through small straws (e.g., about 10 cm long, about 0.5 to 1 cm diameter) onto (1) an open-form pre-concentrator loaded with ATM, and (2) an open-form pre-concentrator loaded with AMA. The sampling time for each pre-concentrator is 5 minutes. The patients tidily breathe about 10 to 15 times during this time period. After the sampling process was complete, each pre-concentrator is eluted by adding about 100 µl methanol. The eluted methanol solutions are collected and directly used for FTICR-MS (ATM conjugate sample) and GC-MS (AMA conjugate sample) analysis without any further processing.

Figure 10:
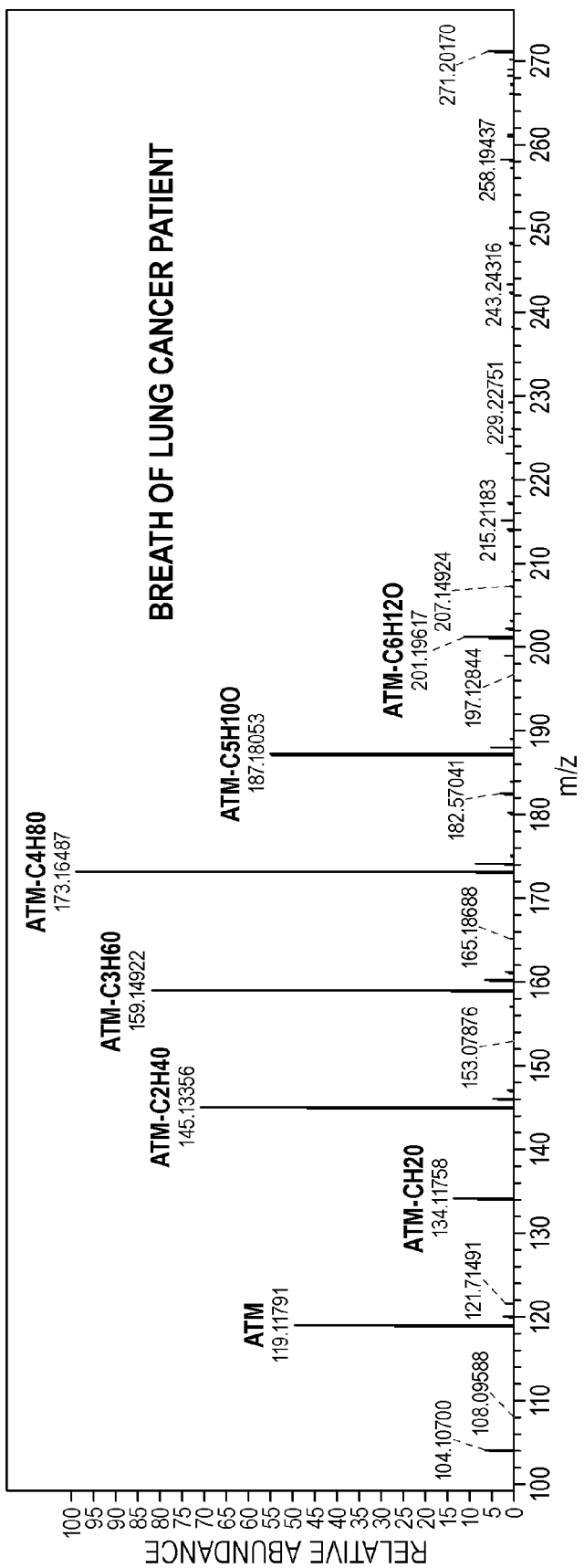
FIG. 10 is mass spectrogram showing an FTICR-MS spectra of a pre-concentrated sample of exhaled breath taken from a lung cancer patient, using an ATM-modified chemical pre-concentrator in accordance with an embodiment of the present invention.
Figure 11:
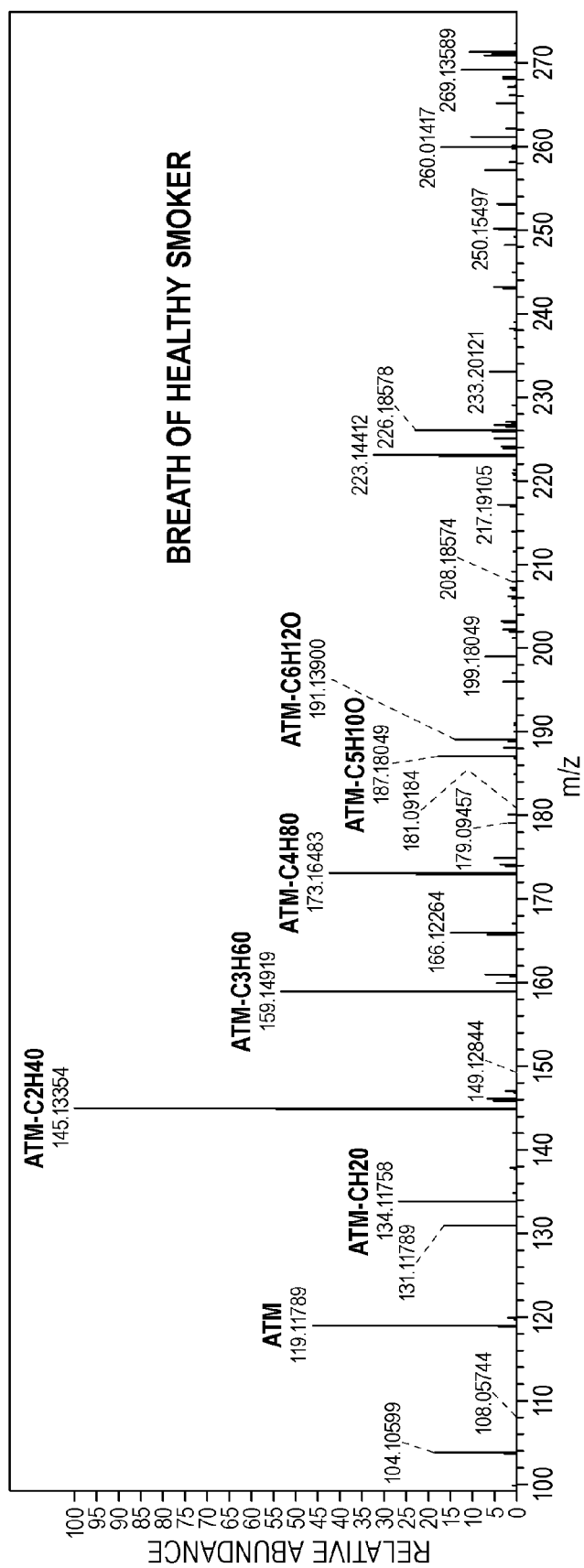
FIG. 11 is mass spectrogram showing an FTICR-MS spectra of a pre-concentrated sample of exhaled breath taken from a healthy smoker subject, using an ATM-modified chemical pre-concentrator in accordance with an embodiment of the present invention.
Figure 12:
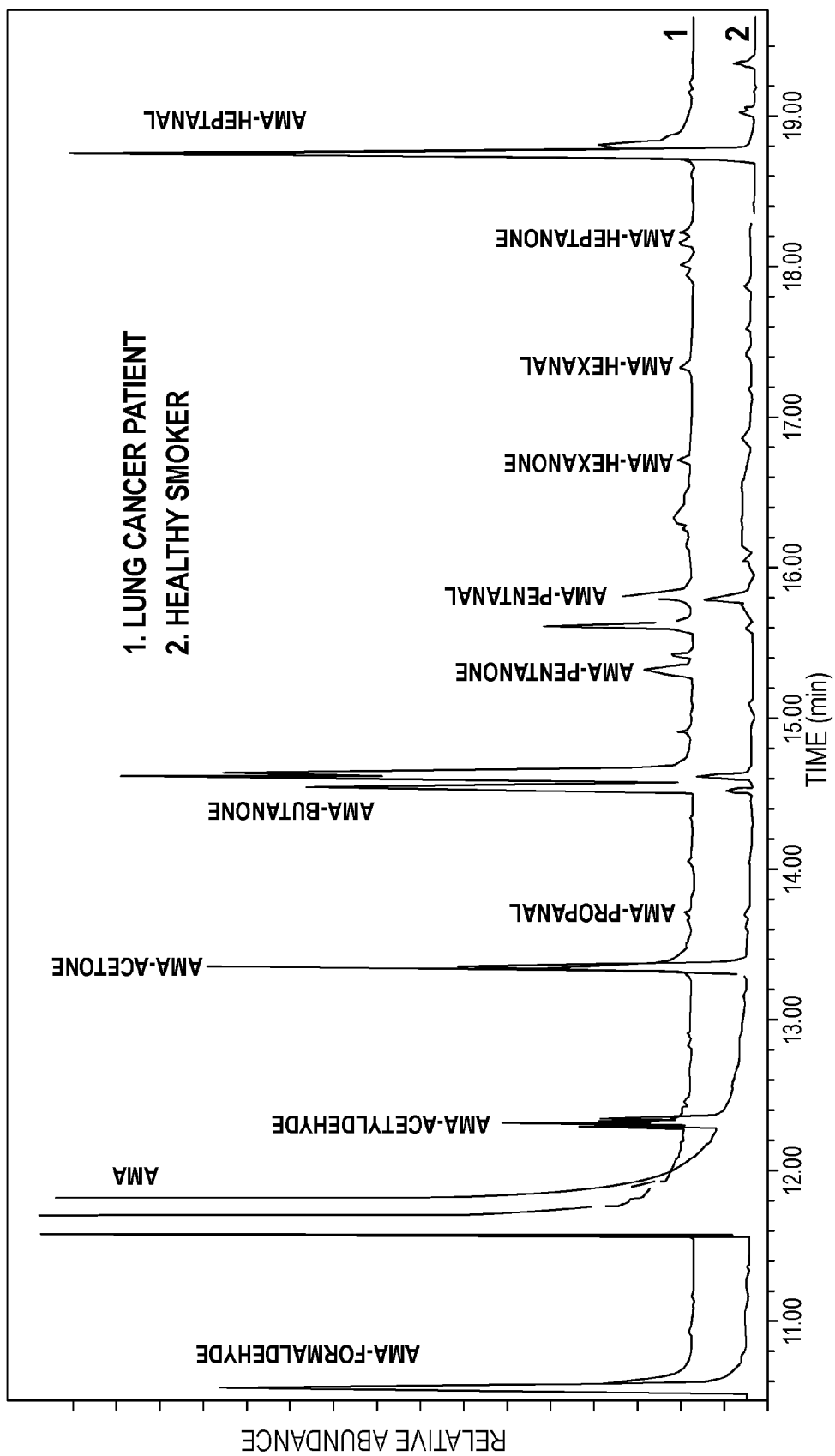
FIG. 12 is mass spectrogram showing over-layed GC-MS spectra of a pre-concentrated samples of exhaled breath taken from a lung cancer patient and a healthy smoker using AMA-modified chemical pre-concentrator in accordance with another embodiment of the present invention.
Figure 13:
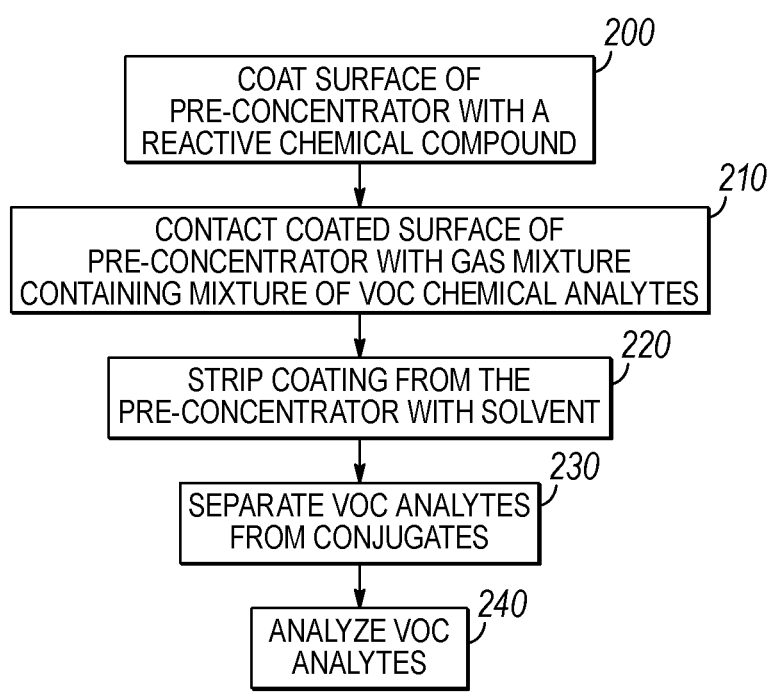
FIG. 13 is a flow-chart illustration depicting an exemplary method to pre-concentrating a broad spectrum of volatile organic compounds (VOCs), in accordance with yet another embodiment of the present invention.

FIG. 10 shows typical FTICR-MS spectra derived from exhaled breath samples of a lung cancer patient and FIG. 11 shows typical FTICR-MS spectra derived from exhaled breath samples of a healthy smoker using the open-form pre-concentrator with ATM coating. Carbonyl compounds from formaldehyde (ATM-$CH_2O$) to dodecyl aldehyde (ATM-$C_{12}H_{24}O$) were detected. Importantly, the pattern of ketone and aldehyde conjugates for the breath of the lung cancer patient and the healthy control are different and distinct. FIG. 12 shows overlayed GC-MS spectra of exhaled breath samples from the cancer patient and the healthy smoker for comparison. In agreement with the FTICR-MS, 2-butanone and n-pentanal in the exhaled breath of lung cancer patients were significantly higher than in healthy smokers. This example demonstrates that the open-form pre-concentrator for breath analysis approach is also suitable for use in testing for lung cancer.

Based on the foregoing, a method of making a chemical pre-concentrator for collecting and pre-concentrating at least one chemical analyte from a dilute gaseous sample is provided. The method includes: contacting a surface of a support structure with a liquid comprising a reactive chemical compound and a solvent; evaporating the solvent to affect forming a layer of the reactive chemical compound on the surface of the support structure, wherein the reactive chemical compound is capable of forming a conjugate with the at least one chemical analyte to thereby retain the at least one chemical analyte on the surface of the support structure.

According to another embodiment, a method of concentrating at least one chemical analyte in a gaseous sample is provided. The method includes contacting a chemical pre-concentrator with a dilute gaseous sample containing the at least one chemical analyte, wherein the chemical pre-concentrator comprises a support structure having a surface, an airflow conduit directed at the surface of the support structure, and a layer comprising a reactive chemical compound on the surface of the support structure; forming a conjugate of the reactive chemical compound and the at least one chemical analyte to retain the at least one chemical analyte on the surface of the support structure, wherein forming the conjugate concentrates the at least one chemical analyte in the chemical pre-concentrator; contacting the chemical pre-concentrator with a solvent; dissolving the conjugate in the solvent to thereby form a concentrated sample of the conjugate; analyzing at least a portion of the concentrated sample to identify or quantify the conjugate.

According to yet another embodiment, a method of diagnosing a disease state of a mammalian patient is provided. The method includes obtaining a biological sample containing a biomarker from the mammalian patient, wherein the biomarker relates to the presence of a disease; contacting a chemical pre-concentrator with a dilute gaseous sample containing the biomarker, wherein the chemical pre-concentrator comprises a support structure having a surface and a layer comprising a reactive chemical compound on the surface of the support structure; forming a conjugate of the reactive chemical compound and the biomarker to retain the biomarker on the surface of the support structure, wherein forming the conjugate concentrates the biomarker in the chemical pre-concentrator; contacting the chemical pre-concentrator with a solvent; dissolving the conjugate in the solvent to thereby form a concentrated sample of the conjugate; analyzing at least a portion of the concentrated sample to identify or quantify the conjugate and the biomarker; and diagnosing the presence of and/or absence of the disease based on the identity or the quantity of the biomarker. In one example, the analyzing includes utilizing Fourier-transform ion cyclotron resonance mass spectrometry (FTICR-MS).

In accordance with yet another embodiment of the present invention, FIG. 12 shows a flow-chart schematic of a method of pre-concentrating a broad-spectrum of VOCs. In Step 200: A layer of a reactive chemical compound is formed on the surface of the micropillars of the support structure to make a pre-concentrator. The layer may also include one or more substances that can facilitate physical adsorption of non-polar or weakly polar volatile organic compounds (VOCs). In Step 210: A gas mixture, which includes a plurality of chemical analytes, with aldehyde or ketone functionality (reactive analytes) and without aldehyde or ketone functionality (unreactive analytes), is passed first through the pre-concentrator coated with reactive chemical compound. Accordingly, the reactive analytes form conjugates with the reactive chemical compounds, while the unreactive analytes may be adsorbed. In Step 220: The reactive chemical compound and the chemical analyte conjugates, along with the adsorbed unreactive analytes will be stripped from the pre-concentrator with a suitable solvent, such as acetonitrile, into a vial. In Step 230: The conjugates may be separated from the unreactive analytes. For example, Fe₃O₄ (iron oxide magnetite) nanoparticles may be added to the acetonitrile solution, to which all the cationic quaternary compound will be adsorbed. Still in Step 230, a magnet outside the vial may separate the black nanoparticle-matrix complex from the solution, enormously reducing the background and solute load, enabling efficient and sensitive analysis by FTICR-MS. Finally, in Step 240, the solution containing the unreactive analytes, substantially free of conjugates and nanoparticles, will be analyzed. The unreactive analytes may be analyzed using GC-MS, by ionizing in negative ion mode using atmospheric-pressure chemical ionization/photoionization (APCI/APPI) at ~10 eV photons, for example, which will not ionize (not detect) the acetonitrile solvent and reject any residual cationic quaternary compounds.

While the present invention has been illustrated by the description of one or more embodiments thereof, and while the embodiments have been described in considerable detail, they are not intended to restrict or in any way limit the scope of the appended claims to such detail. The various features of exemplary embodiments described herein may be used in any combination. Additional advantages and modifications will readily appear to those skilled in the art. The invention in its broader aspects is therefore not limited to the specific details, representative product and/or method and examples shown and described. For example, additional embodiments include, but are not limited to, detecting and analyzing particular chemicals including pollutants, high explosives, and chemical and biological warfare agents. Accordingly, departures may be made from the foregoing details without departing from the scope of the general inventive concept.

What is claimed is:

1. A chemical pre-concentrator for collecting and pre-concentrating at least one chemical analyte from a dilute gaseous sample, the chemical pre-concentrator comprising:
   a support structure having a surface;
   an airflow conduit directed at the surface of the support structure; and
   a layer on the surface of the support structure, the layer comprising a reactive chemical compound having a general formula (I) of

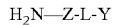
   H₂N—Z-L-Y  (I)

wherein Z is O; L is a linking group; and Y is a di-substituted or tri substituted N or P moiety, wherein the reactive chemical compound is capable of forming a conjugate with the at least one chemical analyte to thereby retain the at least one chemical analyte with the chemical pre-concentrator.

2. The chemical pre-concentrator of claim 1, wherein the surface of the support structure comprises a material selected from the group consisting of dielectrics and semiconductors.

3. The chemical pre-concentrator of claim 1, wherein the support structure comprises a material selected from the group consisting of silicon, polycrystalline silicon, silicon oxide, silicon nitride, silicon oxynitride, silicon carbide, titanium, titanium oxide, titanium nitride, titanium oxynitride, titanium carbide, aluminum, aluminum oxide, aluminum nitride, aluminum oxynitride, and aluminum carbide.

4. The chemical pre-concentrator of claim 1, wherein at least the surface of the support structure comprises silicon oxide, titanium oxide, aluminum oxide, or combinations thereof.

5. The chemical pre-concentrator of claim 1, wherein the surface of the support structure is configured with microchannels, micropillars, pores, or combinations thereof.

6. The chemical pre-concentrator of claim 1, further comprising a housing surrounding said support structure, wherein said housing having an inlet and an outlet, wherein at least one of the outlet or the inlet is configured to couple with a sampling pump to thereby facilitate the transfer of a portion of the dilute gaseous sample outside of the housing into the housing through the inlet.

7. The chemical pre-concentrator of claim 1, wherein Y is a di-substituted or tri-substituted nitrogen to provide the reactive chemical compound having a general formula (II)

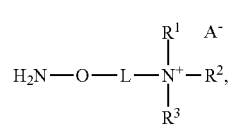

wherein R¹ and R² are independently selected from the group consisting of alkyls, aralkyls, aralkenyls, and aralkynyls, each of which may be substituted or unsubstituted, and optionally contain one or more heteroatoms, or wherein R¹ and R² in combination form a heterocyclic ring;
R³ is selected from the group consisting of H, alkyls, aralkyls, aralkenyls, and aralkynyls, each of which may be substituted or unsubstituted, and optionally contain one or more heteroatoms; and
A is an anionic counter-ion; and wherein said linking group L comprises a non-ionic segment selected from the group consisting of a substituted or unsubstituted alkyl, a substituted or unsubstituted aryl, and an ether.

8. The chemical pre-concentrator of claim 7, wherein R¹, R² and R³ are alkyls, each of which may be substituted or unsubstituted, and optionally contain one or more heteroatoms.

9. The chemical pre-concentrator of claim 7, wherein at least one of R¹, R² and R³ is a methyl group and A is a halide.

10. The chemical pre-concentrator of claim 7, wherein at least one of R¹, R² and R³ is a substituted alkyl including at least two heteroatoms, and the at least one of R¹, R² and R³ has a general formula of -L¹-Z—NH₂, wherein L¹ is a linking group between an ammonium nitrogen and Z.

11. The chemical pre-concentrator of claim 1, wherein Y is a di-substituted nitrogen to provide the reactive chemical compound having a general formula (III)

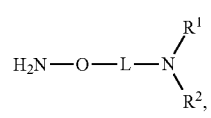

wherein R¹ and R² are independently selected from the group consisting of alkyls, aralkyls, aralkenyls, and aralkynyls, each of which may be substituted or unsubstituted, and optionally contain one or more heteroatoms, or wherein R¹ and R² in combination form a heterocyclic ring.

12. The chemical pre-concentrator of claim 1, wherein the at least one chemical analyte comprises an aldehyde or ketone functional group.

13. A method of concentrating at least one chemical analyte in a gaseous sample, comprising:

contacting the gaseous sample and the chemical pre-concentrator of claim 1; and forming a conjugate of the reactive chemical compound and the at least one chemical analyte to retain the at least one chemical analyte with the chemical pre-concentrator.

14. The method of claim 13, further comprising:

contacting the layer on the surface with a solvent to dissolve at least a portion of the conjugate to form a concentrated sample of the conjugate.

15. The method of claim 14, further comprising analyzing at least a portion of the concentrated sample to identify or quantify the conjugate.

16. The method of claim 13, wherein the at least one chemical analyte comprises an aldehyde or ketone functional group.

17. The method of claim 15, wherein the analyzing at least a portion of the concentrated sample does not use chromatography.

18. The method of claim 15, wherein the analyzing at least a portion of the concentrated sample includes using a mass spectrometer.

19. The method of claim 18, wherein the mass spectrometer uses Fourier- transform ion cyclotron resonance mass spectrometry (FTICR-MS).

20. The method claim 15 further comprising obtaining a gas sample containing the at least one chemical analyte, wherein the at least one chemical analyte is a biomarker relating to the presence of a disease; and diagnosing the presence of and/or absence of the disease by the identifying or the quantifying of the biomarker performed in the analyzing step.

21. The method of claim 20, wherein the biomarker comprises a portion of an isotopically labeled metabolite.

22. A method of diagnosing a disease state in a mammalian patient comprising:

obtaining a biological sample containing at least one chemical analyte from the mammalian patient, wherein the at least one chemical analyte is a biomarker relating to the presence of a disease;

contacting the chemical pre-concentrator of claim 1 with a gaseous sample containing at least a portion of the biological sample;

forming a conjugate of the reactive chemical compound and the biomarker to retain the biomarker with the chemical pre-concentrator; and performing analysis of the conjugate to identify and/or quantify the biomarker.

23. The method of claim 22, further comprising:

contacting the layer on the surface with a solvent to dissolve at least a portion of the conjugate to form a concentrated sample of the conjugate.

24. The method of claim 23, further comprising analyzing at least a portion of the concentrated sample to establish the identity or quantity of the conjugate and/or the biomarker; and diagnosing the presence of and/or absence of the disease based on the identity or the quantity of the biomarker.

25. The method of claim 24 wherein the analyzing at least a portion of the concentrated sample includes using a mass spectrometer.

26. The method of claim 25, wherein the mass spectrometer uses Fourier-transform ion cyclotron resonance mass spectrometry (FTICR-MS).

* * * * *